(12) United States Patent
Formichi (10) Patent No.: US 8,343,087 B2
(45) Date of Patent: Jan. 1, 2013

(54) PROSTHETIC DEVICE FOR CREATING A VASCULAR BYPASS, WITHOUT CLAMPING, FROM A BLOOD VESSEL

(75) Inventor: Maxime Formichi, Marseilles (FR)

(73) Assignee: Vascular Office (Sarl), Marseille (FR)

( * ) Notice: Subject to any disclaimer, the term of this patent is extended or adjusted under 35 U.S.C. 154(b) by 171 days.

(21) Appl. No.: 12/919,854

(22) PCT Filed: Feb. 25, 2009

(86) PCT No.: PCT/FR2009/000201
§ 371 (c)(1),
(2), (4) Date: Oct. 5, 2010

(87) PCT Pub. No.: WO2009/112721
PCT Pub. Date: Sep. 17, 2009

(65) Prior Publication Data
US 2011/0021969 A1    Jan. 27, 2011

(30) Foreign Application Priority Data
Feb. 28, 2008    (FR) ...................................... 08 01104

(51) Int. Cl.
*A61M 5/00* (2006.01)
*A61F 2/06* (2006.01)
(52) U.S. Cl. ........... 604/8; 606/153; 606/154; 623/1.14; 623/1.27; 623/1.36

(58) Field of Classification Search ................. 623/1.14, 623/1.27, 1.36
See application file for complete search history.

(56) References Cited

U.S. PATENT DOCUMENTS

| | | | | |
|---|---|---|---|---|
| 5,893,369 A | * | 4/1999 | LeMole | 606/184 |
| 6,395,015 B1 | * | 5/2002 | Borst et al. | 606/213 |
| 6,485,513 B1 | * | 11/2002 | Fan | 623/1.36 |
| 6,503,258 B1 | | 1/2003 | Filho | |
| 7,189,257 B2 | * | 3/2007 | Schmitt et al. | 623/1.51 |
| 2002/0116016 A1 | * | 8/2002 | Barath | 606/153 |
| 2009/0036817 A1 | * | 2/2009 | Dakin et al. | 604/8 |

FOREIGN PATENT DOCUMENTS

EP    0269254 A    6/1988

* cited by examiner

*Primary Examiner* — Melanie Hand
*Assistant Examiner* — Joshua Lee
(74) *Attorney, Agent, or Firm* — Egbert Law Offices, PLLC (57) ABSTRACT

A prosthetic device for creating a vascular bypass from an arterial vessel has at least one prosthetic tube joined to an orifice of a flexible collar. The prosthetic tube extends from an outer face of the collar. The collar has an inner face surface for attachment to the arterial vessel. The collar has a connection zone has an annular cavity extending around and away from the orifice. The annular cavity is suitable for receiving an injected glue or bioabsorable haemostatic product so as to attach to the arterial vessel.

20 Claims, 9 Drawing Sheets

PROSTHETIC DEVICE FOR CREATING A VASCULAR BYPASS, WITHOUT CLAMPING, FROM A BLOOD VESSEL

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention concerns a prosthetic device for creating a vascular bypass, without clamping, from a blood vessel, in particular from the aorta, which may have significant collateral branches. More particularly, the invention relates to a prosthesis for vascularization of the collateral branches of the aorta, without clamping, that is, without interrupting blood flow within it by means of occlusive forceps or clamps, or other means.

2. Description of Related Art Including Information Disclosed Under 37 CFR 1.97 and 37 CFR 1.98.

For this purpose, whenever we wish to supply blood to an artery that emerges from the aorta because it is more or less completely occluded, several procedures are used, more or less preferentially, depending on the pathological circumstances.

When the artery presents a stricture or isolated and short occlusion, a method using balloon dilatation together with the insertion of an endoprosthesis, is recommended. This endoprosthesis (still referred to as a stent) is a kind of mesh tube intended to keep the dilated area that was the site of the lesion permeable. This method is noninvasive. It involves the use of catheters introduced into the arteries, most frequently under local anesthesia. There is no surgical incision. Bleeding is practically nonexistent.

The disease is often more developed, affecting a considerable length of a branch of the aorta, or several branches, and may even affect the portion of the aorta from which those branches emerge. It may then be necessary to supply blood to the organs irrigated by this, or these, artery(ies) through the use of one or more vascular bypasses originating at the aorta. These bypasses consist, in general, of prosthetic conduits. They allow lesions to be short-circuited. One of the ends of the prosthetic conduit, known as the proximal end, is sewn to the aorta. This is the extremity that captures the blood. The other extremity, known as the distal end, is sewn to the branch of the aorta downstream from the lesions. It is this extremity that distributes the blood. The sewn areas are referred to as anastomosis.

Proximal anastomosis of the aorta is performed by sewing the prosthetic tube to an orifice cut in the wall of the aorta. This orifice, specifically known as an aortotomy when it involves the aorta, must be isolated from circulation for as long as it is being sewn to avoid bleeding. To do this, circulation in the aorta is stopped by means of special forceps known as clamps. Clamping may either be total, in which case circulation is completely stopped, or partial, which allows some blood to flow to those areas located downstream. Similarly, distal anastomosis of the collateral branch occurs by isolating from circulation the segment of the artery that is the site of the anastomosis and by making an opening therein or by sectioning.

These bypass procedures have existed for several decades. They necessitate:

First, a surgical incision of the abdominal wall and/or thoracic wall, depending on circumstances, to access the aorta and, sometimes, another incision (or several) to access the branch (or branches) one wishes to revascularize.

Second, partly or completely stopping circulation in the aorta to make the suture or anastomosis of the prosthetic tube at that location. Any complete or partial stoppage of circulation in the aorta will have significant hemodynamic and metabolic repercussions on all organs located downstream and upstream.

Downstream: the organs will be more or less completely deprived of blood and, therefore, of oxygen, for the entire duration of the anastomosis. This cessation of circulation is more or less harmful depending on where the cessation of circulation occurs.

For example, stopping circulation at the terminal part of the aorta located in the abdomen can easily be tolerated for several hours. Downstream, there remain only the inferior members and the organs of the minor pelvis, which are relatively insensitive to what is referred to as the absence of circulation or ischemia (oxygen deprivation).

However, as circulation is stopped higher (upstream) on the aorta, tolerance is reduced.

Therefore, if circulation is stopped near the lower part of the thorax, a portion of the spinal cord is deprived of arterial blood, as well as all the organs located in the abdomen, such as, for example, the kidneys, liver, and digestive tract. These organs can support ischemia for no more than some tens of minutes at the most. Consequently, the time during which the anastomosis can be carried out is very limited.

The most harmful consequences are found when circulation is stopped near the origin of the aorta, just after it emerges. In addition to depriving the other areas previously mentioned, which are located downstream, this portion of the aorta gives rise to arteries that irrigate the brain. These arteries can tolerate no more than two or three minutes of circulatory arrest, which makes it impossible to carry out the anastomosis. Consequently, circulation can only be stopped in this region by making use of techniques of extracorporal circulatory assistance involving the use of machines. Such means, used during suturing, continue to provide blood to the brain and to the areas previously mentioned in order to eliminate the deleterious effects of stopping circulation in the aorta to implant the prosthetic bypass. Unfortunately, such techniques of circulatory assistance are complicated. They are in themselves the cause of inherent complications and significant mortality.

Upstream, the consequence of interrupting arterial flow results in hypertension, which is manifested in the region situated above. As with ischemia, hyperpressure increases the higher up one works. It makes the heart work harder.

Third, suturing the prosthetic tube and aorta wall edge to edge with a very fine thread. When circulation is restored to the attachment area, there is a risk of hemorrhage. For, it is rare for a suture to be initially leakproof and circulation must often be interrupted again and stitches added to the suture. This factor needs to be examined very carefully today because of the frequency of antiaggregating and anticoagulating treatments that are practically ubiquitous and prescribed for life for patients afflicted by cardiovascular diseases. These treatments, which increase the risk of bleeding, cannot always be stopped during the operation.

On the other hand, we note that this type of edge-to-edge suture has other drawbacks, especially over the long term. The suture is continually subject to arterial pressure with a momentary increase 70 times a minute due to the contraction of the heart. Occasionally there are tears, either in the aorta wall or in the prosthesis, with separation of the connection between artery and prosthesis. This separation, once begun, will continue to develop through the effect of arterial pressure. In approximately 2% of cases it leads to the formation of a false aneurysm that most often requires a new operation.

Fourth, suturing the distal end of the prosthetic tube on the collateral branch or branches for which blood is destinated. This part of the operation is less traumatic than the aortic suture.

Prosthetic devices have been proposed to facilitate anastomosis and limit certain risks (FR-2799362, EP-0269254, U.S. Pat. No. 6,273,912, WO-2006/013234, FR-2751867). These devices comprise a prosthetic tube, generally made of a synthetic textile compatible with biological tissues and, therefore, referred to as "biocompatible," that may or may not include one or more ramifications, and is equipped, at its extremities, with a collar suitable for anastomosis of said prosthetic tube on an organic conduit such as an artery (aorta or other) and/or a vein. These collars allow the prosthesis to be attached to one or two organic conduits by means of a conventional suture or by using clips or staples opposite openings (arteriotomies) made in said organic conduit or conduits. In all cases, the inner face of these collars is in contact with the interior of the blood vessel and the circulating blood.

However, the operating procedure employing these prosthetic devices always requires clamping or the interruption of blood circulation in the portion of the anatomical conduit in which the prosthesis is to be implanted, along with the serious consequences this may entail, while the risk of peroperative and postoperative bleeding remains significant.

An object of the present invention consists of a prosthetic device that can be attached to an artery, in particular to the aorta, without the clamping that stops circulation and without the risk of peroperative and postoperative bleeding.

BRIEF SUMMARY OF THE INVENTION

According to a characteristic feature, the first objective mentioned above is achieved through the use of a prosthetic device comprising one or more prosthetic tubes one of whose extremities is connected to a flexible attachment collar having an outer face and an inner face intended to be applied to the external wall of said arterial vessel. This collar being provided with one or more orifices arranged in a central zone known as the orifice zone, which orifices communicate with said prosthetic tube or tubes. This collar having a connection zone arranged around said orifice zone, at a distance from the edge of said orifice or orifices and intended to be attached to the outer wall of an arterial vessel. The inner face of this connection zone being provided with at least one means for creating an annular sealing zone around said orifice zone.

According to a first embodiment, the inner face of the connection zone has at least one flexible annular seal arranged around the orifice zone.

According to a second embodiment, the connection zone has, on its inner face, a space or annular cavity around the orifice zone, allowing a product to be injected, for example, a glue and/or a preferably bioabsorbable haemostatic product, intended to serve as an annular attachment area forming a leakproof seal.

According to a preferred embodiment, the annular seal is made of silicone or polyurethane.

According to a possible embodiment, the annular cavity is delimited laterally by two spaced concentric seals.

According to another characteristic feature, the annular cavity is delimited by a permeable lower annular strip intended to be applied to the wall of a blood vessel, in particular the aortic wall, this annular strip being provided with small holes allowing for the diffusion, on the underside of said collar, of a biological glue and/or a haemostatic product injected into said cavity.

According to another characteristic feature, the annular cavity includes a strip of biocompatible material provided with small holes and attached along its lateral edges to the lower face of the collar.

According to an interesting embodiment, the annular strip constituting the lower face of the cavity is made of a bioabsorbable material.

According to another embodiment, the annular cavity is arranged on the outside of the flexible seal.

According to another embodiment, the underside of the collar has an annular seal arranged on the outside of the annular cavity.

According to an interesting embodiment, at least one flexible catheter is arranged in the annular cavity for injecting a biological glue and/or a haemostatic product, the proximal end of the catheter crossing a hole formed in the collar and accessible from the outer face of the latter so as to enable its connection to a reservoir of biological glue and/or haemostatic product and its withdrawal during the injection of the aforementioned products.

According to an advantageous arrangement, two flexible catheters are arranged, in inverse relationship, in the cavity formed on the underside of the attachment collar, one for injecting a biological glue, the other for the injection of a catalyzing product, said catheters being capable of successive withdrawal by following inverse paths (clockwise and counterclockwise).

According to another characteristic arrangement, the inner face or lower face of the collar presents an annular thickening around the orifice zone, between this zone and the location of the annular cavity.

The invention primarily helps avoid the cessation of blood flow in the aorta during the operation and reduces the risk of bleeding when the collateral branches of the aorta are revascularized with a bypass off the latter. This result is due to the method of attachment of the collar on the wall of the aorta, which takes place without any breach of this latter.

These solutions help reduce the impact of the operation and thereby eliminate the mortality inherent in circulatory arrest and bleeding.

The device of the invention can also be applied to the revascularization of the branches of the aorta whenever these emerge from a pathological aorta presenting what is known as an aneurysm. Under these conditions, the portion of the aneurysmic aorta must be replaced and arterial circulation in the collateral branches must be quickly reestablished. The device of the invention can be used to revascularize the branches of the aorta with the benefits already described. Replacement of the diseased portion of the aorta can be carried out after this revascularization. This replacement can, depending on the anatomy of the aneurysm, involve surgery or, preferably, the insertion of an aortic endoprosthesis. With the latter solution, which is the least aggressive for the patient, the procedure makes use of a minimally invasive technique using a catheter. The presence of the prosthetic device of the invention previously implanted upstream or downstream on the aorta can also facilitate the insertion of the endoprosthesis. It is, in effect, possible to use one of the prosthetic tubes to introduce the endoprosthesis into the aorta without having to introduce the catheter through the femoral pathway. This is an additional advantage that will be described in greater detail below.

BRIEF DESCRIPTION OF THE DRAWINGS

The above objectives, characteristics and advantages, along with others, will be better appreciated from the following description and the attached drawings in which.

Reference is made to the above drawings to describe interesting embodiments of the prosthetic device according to the invention, these being in no way limiting.

DETAILED DESCRIPTION OF THE INVENTION

This device comprises at least one flexible prosthetic tube or conduit 1a, one of whose ends is connected to flexible collar 2 having an outer face 3 and an inner face 4. Depending on the application, the device can have several prosthetic tubes. Notably, when used to revascularize collateral branches of the aorta, this device has three flexible prosthetic tubes or conduits, 1a, 1b, 1c, attached to flexible collar 2. It may have more than three flexible prosthetic tubes or conduits, for example, four tubes or conduits.

The central portion of flexible collar 2 is provided with one or more orifices 5, the number of which corresponds to the number of prosthetic conduits 1a, 1b, 1c. Based on the examples shown, collar 2 is supplied with three orifices, 5a, 5b, 5c, each of which communicates with one of prosthetic conduits 1a, 1b, 1c, respectively.

The shape of flexible collar 2 is such that it makes close contact with the outer wall of the arterial vessel on which it is to be attached.

Thus, the shape and dimensions of flexible collar 2 may vary with the shape and size of the anatomical conduits at the location where it is desirable to insert the prosthetic device. This shape is approximately that of a portion of a straight cylinder with rounded angles when the device must be inserted on a rectilinear portion of the aorta or that of a bent cylindrical portion, more or less curved, whenever said device must be connected to the curved portion of the aorta known as the aortic arch.

Flexible collar 2 is made of prosthetic materials commonly used for vascular prostheses, such as, for example Dacron (registered trademark) or other similar polyester, PTFE (for example, Gore-tex, registered trademark), polyurethane, or any other biologically compatible material.

As indicated above, flexible collar 2 may be provided with more than three prosthetic conduits, in which case it is also provided with more than three orifices.

Figure 5:
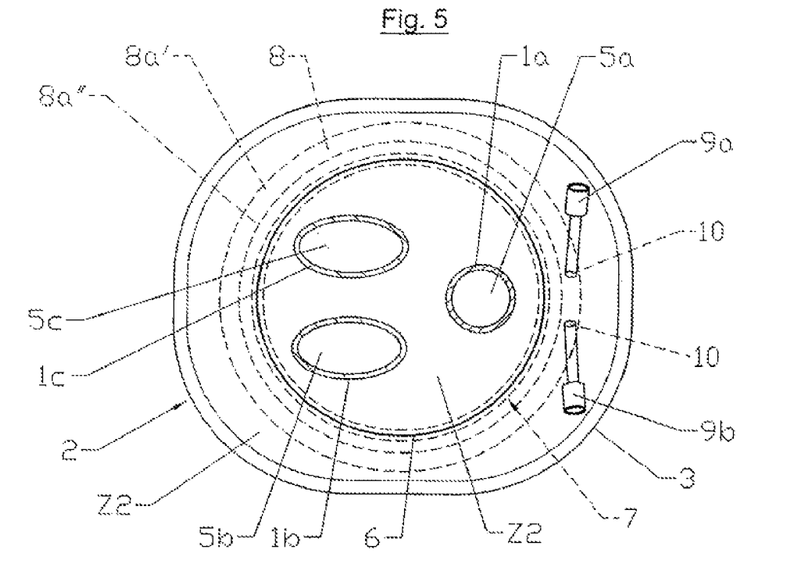
FIGS. 5 and 6 are views similar to FIGS. 3 and 4, respectively, illustrating a variant embodiment of the prosthetic device.
Figure 6:
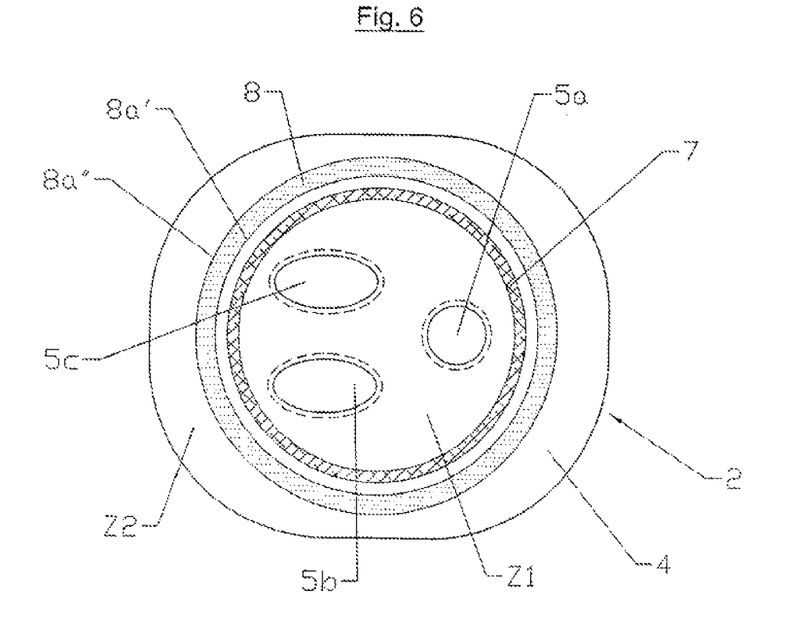
Figure 7:
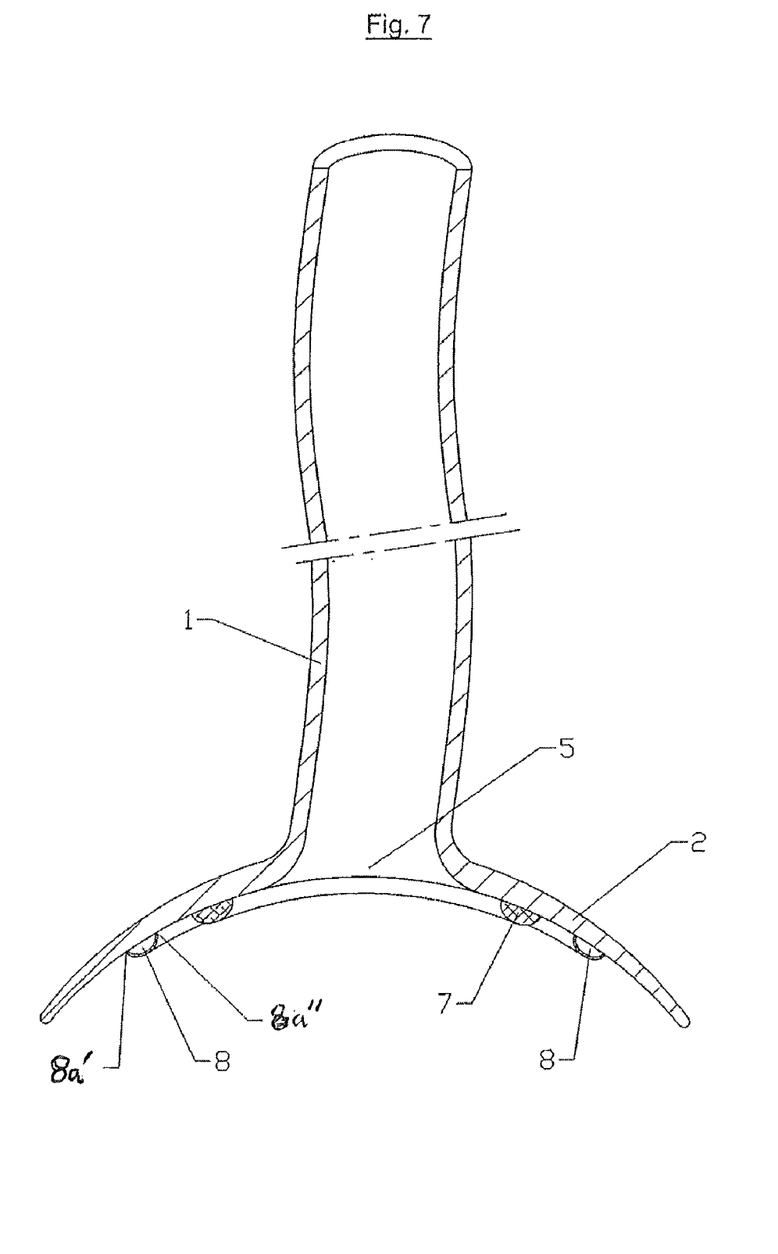
FIG. 7 is a larger scale section along line 7-7 of FIG. 3.
Figure 8:
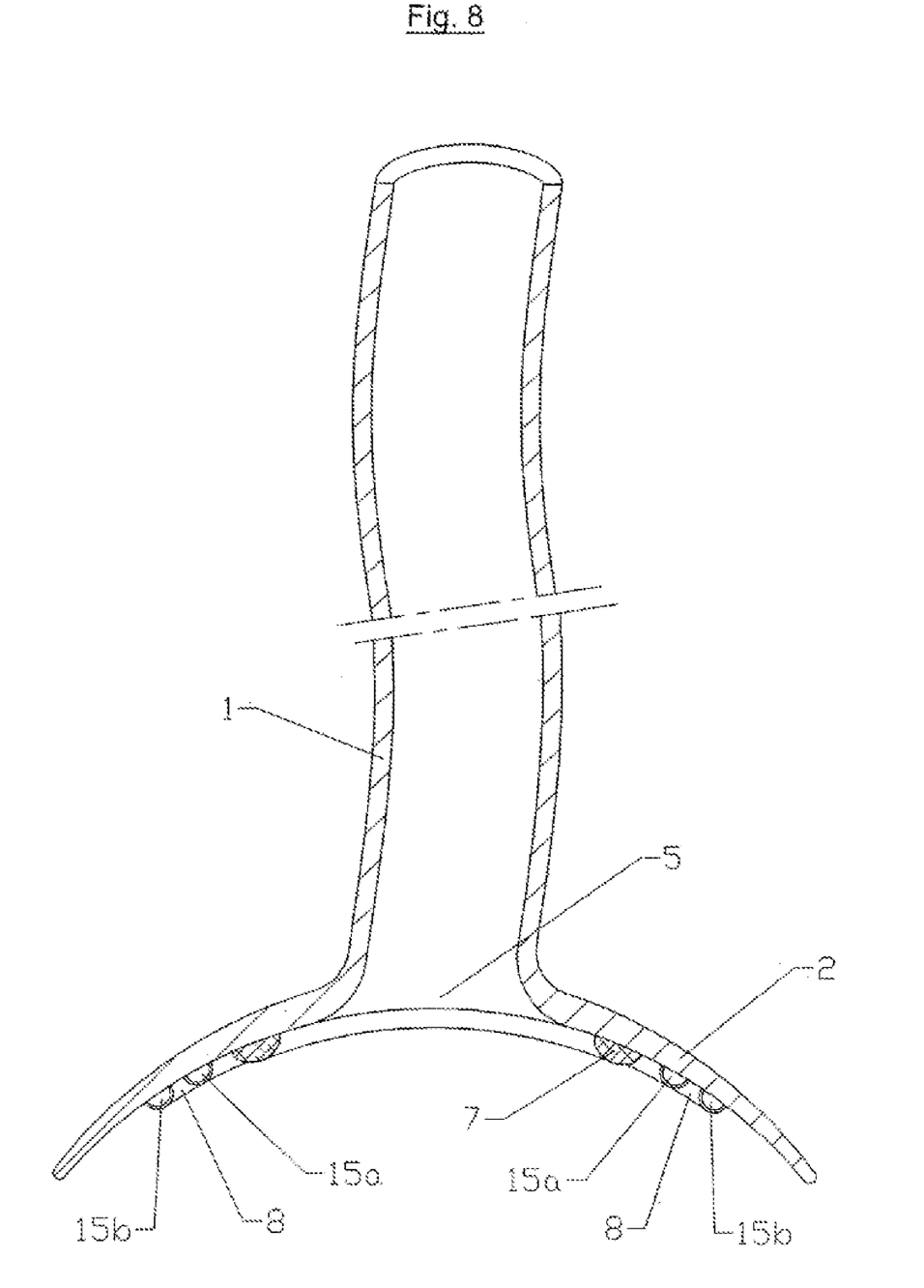
FIGS. 8 and 9 are views similar to FIG. 7, and illustrate two variant embodiments of the surface of the attachment collar.

As indicated above, this collar, provided with orifices 5a, 5b, 5c, has two opposed faces, namely:
an outer face, 3, visible after insertion of the device and
an inner face, 4, intended to be placed in contact with the aorta Orifices 5a, 5b, 5c, can be aligned regularly along the median portion of the collar (FIGS. 1 to 4) corresponding to the axis of the vessel and to circulation, or placed differently (FIGS. 5 and 6). Regardless of their arrangement, they occupy the central zone of the collar, known as the orifice zone, Z1, in the remainder of the description. The part of the collar situated around orifice zone Z1 is intended to be connected to the wall of the aorta and is known as the connection zone, Z2, which is found at a distance from the edge of orifice(s) 5a, 5b, 5c.

Each orifice 5a, 5b, 5c, is extended by prosthetic tube 1a, 1b, 1c, whose size or section is equivalent to that of the artery to be revascularized. Prosthetic tube 1a, 1b, 1c is connected to the edge of the corresponding orifice 5a, 5b, 5c by means of a threaded suture, by gluing, thermal welding, or any other appropriate procedure that provides the necessary seal and solidity. The angle of insertion of prosthetic tube 1a, 1b, 1c near an orifice 5a, 5b, 5c may be comprised between 1° and 90°. The shape of the orifice or of each orifice is adapted to the angle of insertion in order to obtain the best blood hemodynamics. The orifice may be circular in shape for insertion of the prosthetic tube close to 90°; it may have a more or less pronounced oval shape if the angle of insertion of the prosthetic tube on the collar is less than 90°. In the latter case, the major axis of the oval orifices may have different orientations depending on the direction of the prosthetic conduits based on the location of the connection of the distal end of said conduits on the collateral branches of the aorta.

The length of prosthetic tubes 1a, 1b, 1c connected to the edge of orifices 5a, 5b, 5c will be adapted to the distance involved in joining the revascularized artery.

Orifice zone Z1 is preferably delimited by colored mark 6 visible on the outer face of the collar. Depending on the arrangement of the orifices, this mark will be more or less circular or oval in shape.

It will be circular in shape whenever the three orifices are grouped in a triangular zone in the center of the collar. This circular colored mark may pass through the three angles of a triangle or slightly more on the outside. It will be oval in shape if the orifices are aligned with one another. Regardless of the arrangement of the orifices, colored mark 6 will surround orifice zone Z1, leaving an annular space between itself and the edge of said orifices. This colored mark serves as the limit between orifice zone Z1 and peripheral connection zone Z2, intended to be connected to the aorta.

This mark or colored line 6 serves as a reference for making suture stitches, which will follow this line during attachment.

Figure 9:
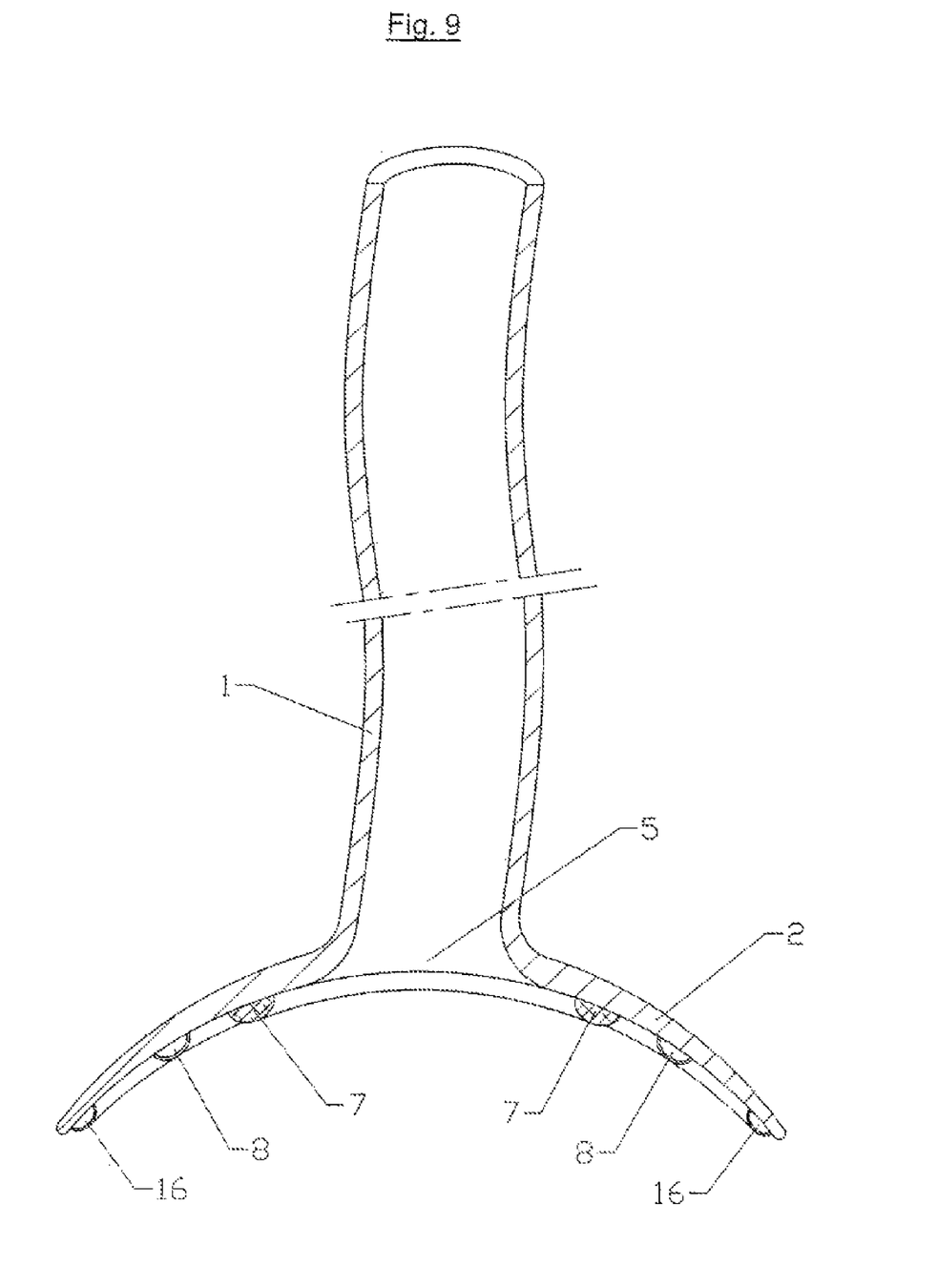

Inner face 4, in correspondence with colored mark or line 6 visible on the outer face, is provided with an annular thickening or swelling 7, employed to serve as a leakproof seal. Leakproof seal 7 describes, along inner face 4, the same path as colored mark 6 visible on the outer face or upper face 3, so that the first suture that will be made by following the path of outer colored mark 6 will apply this seal 7 to the arterial wall and seal this suture when circulation has been established in prosthetic conduits 1a, 1b, 1c. When thus made, the suture is located at a distance from the orifices that will then be created during a subsequent and quite distinct period of the operation on the wall of the aorta. This suture distant from the orifices (lack of edge-to-edge suture) will later create a kind of natural valve V (FIG. 10) on the wall of the aorta that will be applied to the wall of the collar through the effect of arterial pressure. This particular arrangement, obtained after there is circulation in the prosthetic device, isolates the suture zone and helps increase the tightness of the seal (FIG. 9).

Seal 7 may include a strip of Teflon®, Dacron®, PTFE, or other flexible biocompatible material. It may preferably be made of a material such as silicone or polyurethane, which can easily be connected to inner face 4 of collar 2, and which has the characteristics of flexibility needed to fulfill the function or role of a seal.

Figure 1:
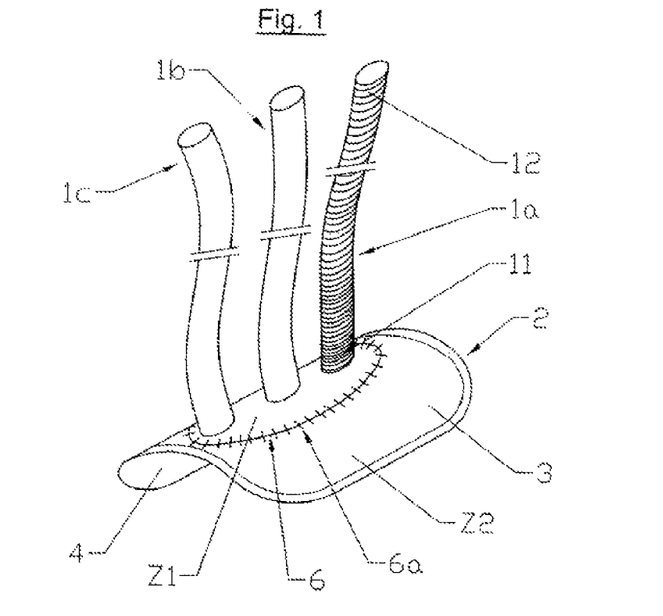
FIG. 1 is a perspective view of an embodiment of the prosthetic device according to the invention that, in this example, has three collateral branches or prosthetic conduits.
Figure 2:
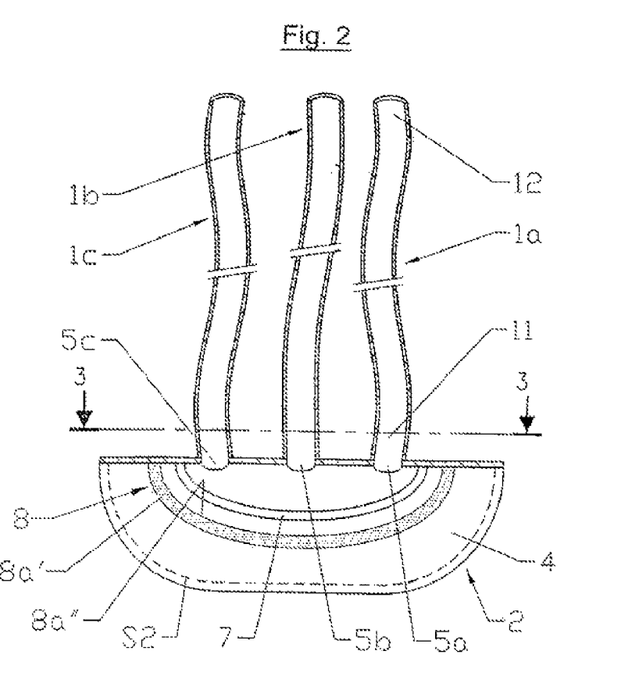
FIG. 2 is cutaway section of this device.
Figure 3:
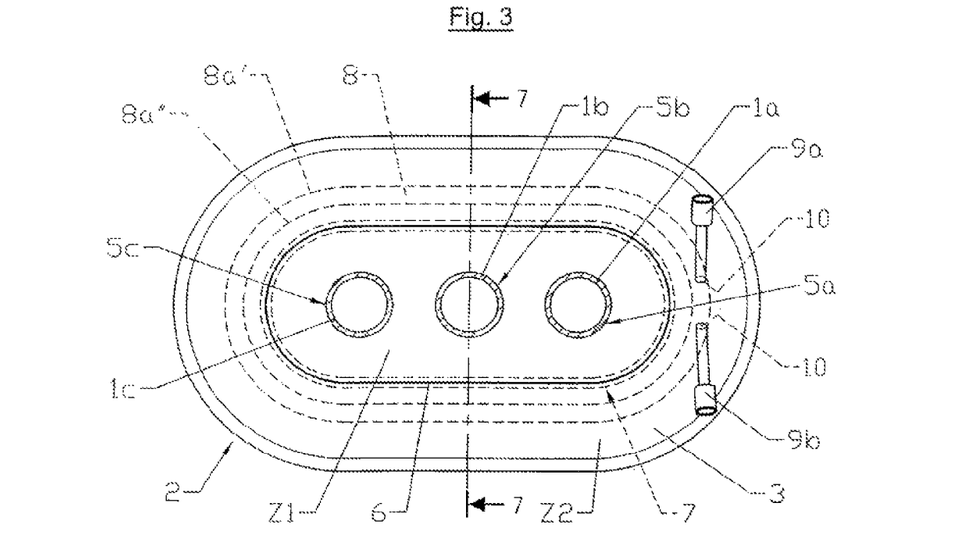
FIG. 3 is a top view and section along line 3-3 of FIG. 2 showing the outer face of the attachment collar of the device.
Figure 4:
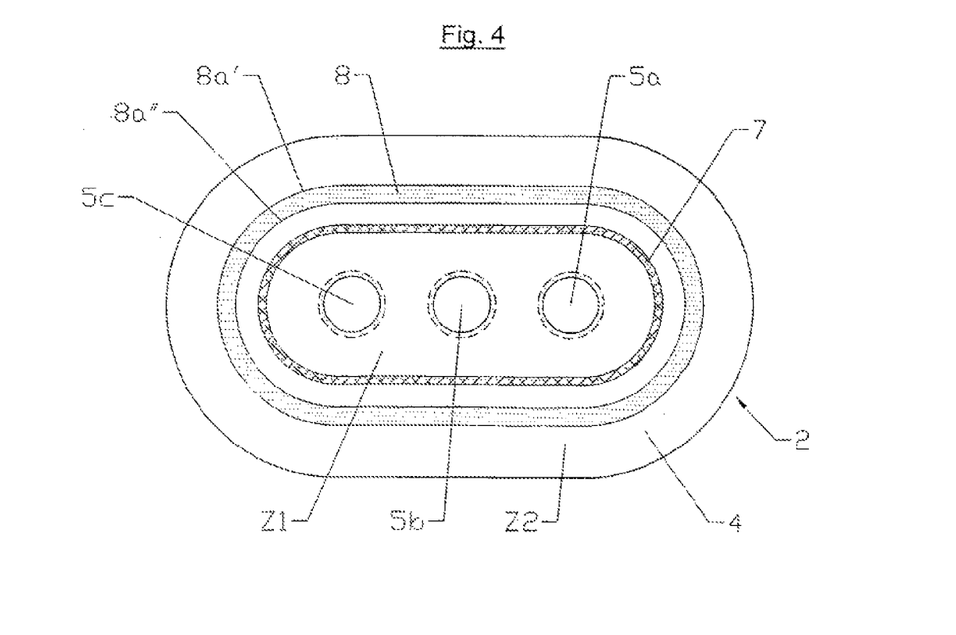
FIG. 4 is a bottom view showing the inner face of this collar.

The recommended placement of suture stitches along colored line 6 can be indicated by small transverse markings, 6a, arranged uniformly along the path of said colored line (FIG. 1). In connection zone Z2 and beneath lower face 4 of collar 2, a cavity or annular channel 8 is formed around orifice zone 5a, 5b, 5c . . . This cavity 8 is delimited by an annular strip of biological material, preferably bioabsorbable. This strip of material is provided with small holes and connected, along its lateral edges, 8a', 8a", to lower face 4 of collar 2 constituting the upper wall of said cavity. This latter, located on the underside of collar 2, is intended to allow the injection of biological glue and/or a haemostatic product during the attachment process, in such a way that said glue or said haemostatic product crosses permeable wall 8a of cavity 8 and is applied to the wall of the aorta, constituting an alternative or supplementary attachment zone and an impermeable barrier around the orifice zone and, ultimately, around seal 7.

Preferably, at least one flexible catheter, 9a, is arranged in annular cavity 8 to facilitate the injection of biological glue and/or haemostatic product. The proximal end of this flexible catheter is equipped with an element that connects to a reservoir of glue and/or haemostatic product (not shown), crosses opening 10 formed in collar 2 and is accessible from the exterior of this [collar] so as to permit its connection to said reservoir, followed by its withdrawal during the injection of the glue and/or haemostatic product.

Whenever the glue consists of a substance that requires its association with a catalyst, a second catheter, 9b, is arranged in annular cavity 8, positioned inversely to first catheter 9a. This second catheter 9b has a proximal end that is provided with a connection element also crosses a second opening, 10, formed in collar 2. It is intended to allow a catalyzing product to be injected into cavity 8. During the injection of glue and catalyzing product, catheters 9a and 9b are successively withdrawn by following opposite paths (clockwise and counterclockwise).

Catheter 9a and catheter 9b allow glue and catalyzing product to be injected as they are being withdrawn from cavity 8.

When cavity 8 has been filled with glue, possibly catalyzed, it diffuses to the aortic wall through the small orifices in permeable lower wall 8a of cavity 8. This diffusion of glue through the small orifices of lower wall 8a of cavity 8 allows collar 2 to be securely and impermeably attached to the wall of the aorta, which is completed by the action of seal 7.

According to a possible embodiment, cavity 8 may be delimited by two spaced concentric flexible seals, 15a, 15b, made of biocompatible material, for example, silicone or polyurethane, positioned on inner face 4 of the collar.

In such a case, injection of the glue and/or haemostatic product occurs after attachment of the collar by suturing the collar to the arterial wall. Injection takes place through at least one opening or orifice, 10, terminating in cavity 8, and formed, for that purpose, in the collar.

Supplementary annular seal 16, similar to seals 7, 15a, 15b, can be arranged on the outside of annular cavity 8, on the inner face 4 of collar 2, for example, near the edge of said collar. This supplementary annular seal corresponds to a second colored mark visible on the outer face of the collar in a manner identical to that described for first flexible seal 7 and having the same characteristics, to facilitate suturing.

All these multiple seal or attachment elements, situated in peripheral connection zone Z2 around zone Z1 will be more or less combined with one another, allowing the collar to be attached to the aorta over a large surface, considerably increasing the resistance of the attachment compared to a conventional edge-to-edge suture.

As an example, we have shown a prosthetic device comprising three collateral branches or prosthetic conduits, 1a, 1b, 1c. Again, we wish to emphasize that the prosthetic device according to the invention may have a single collateral branch, or two branches, even more than three branches.

Branches 1a, 1b, 1c, may preferably be made of a prosthetic material identical to that with which collar 2 is made, or compatible with uninterrupted fabrication of said collar.

When collateral prosthetic branches 1a, 1b, 1c are fabricated of Dacron®, they will preferably be crimped, as is customary for prosthetic conduits to make them flexible, variable in length, and to avoid wrinkles. These branches will be sufficiently long so they can reach the vessels emerging from the aortic arch, or any other portion of the aorta, from the site where the device is implanted.

The diameters of collateral prosthetic branches 1a, 1b, 1c can be identical to one another or specifically adapted to the diameter of each artery to be revascularized.

They have a proximal part 11 connected to outer face 3 of the collar and a distal part 12 intended to be anastomosized with the vessels being revascularized by a conventional surgical technique.

Figure 13:
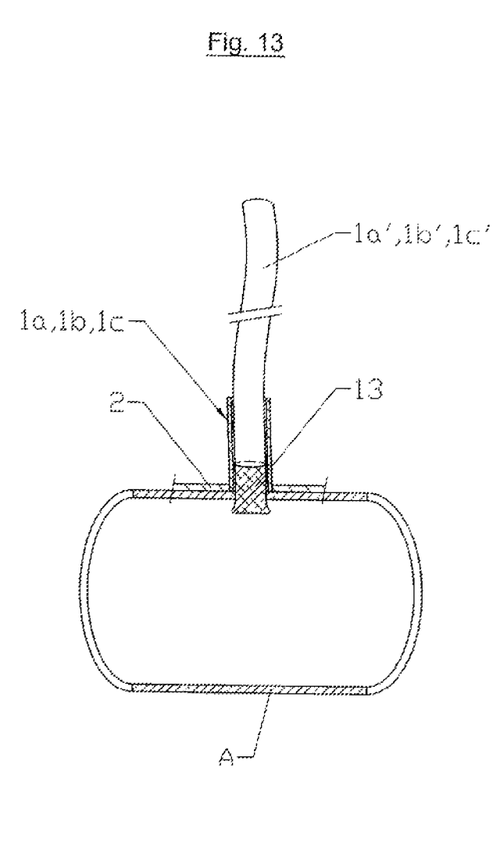
FIG. 13 is a partial cutaway view showing another embodiment of the prosthetic conduits.

According to another possible embodiment, the prosthetic tubes or conduits, 1a, 1b, 1c, are intentionally short (for example, on the order of four to five centimeters). They will subsequently be extended by tube segments 1a', 1b', 1c' (FIG. 13) of a size suitable for connecting to the artery to be revascularized A1, or A2, or A3.

The two tube segments 1a-1a', 1b-1b', 1c-1c', can be connected to one another by a suture or through the use of a stent integral with the proximal end of tube 1a', 1b', 1c' used to extend the short prosthetic tubes. On FIG. 13 an extension tube segment (1a', 1b', 1c') is shown, connected by means of a stent (13) to a short prosthetic conduit (1a, 1b, 1c) issuing from collar 2.

The prosthetic branches can be integral with the outer face or upper face 3 of collar 2 by weaving, or continuous knitting, or by a simple suture.

Below is described an operating method using the prosthetic device according to the invention to realize a vascular bypass from the aorta without interrupting blood circulation in the latter.

Unlike a conventional vascular prosthesis that is sewn to the edges of a previously prepared aortic orifice, the collar of the device according to the invention is attached to the wall of an intact, circulating portion of the aorta. At the moment of attachment, there is no communication between the aorta and the exterior, as is the case with the use of a conventional prosthesis.

This feature allows suturing without requiring any interruption of circulation, partial or total, at the aorta. Thus, during suturing, blood continues to circulate normally downstream. This avoids harm to downstream organs deprived of blood and the use of a technique of circulatory assistance.

Figure 10:
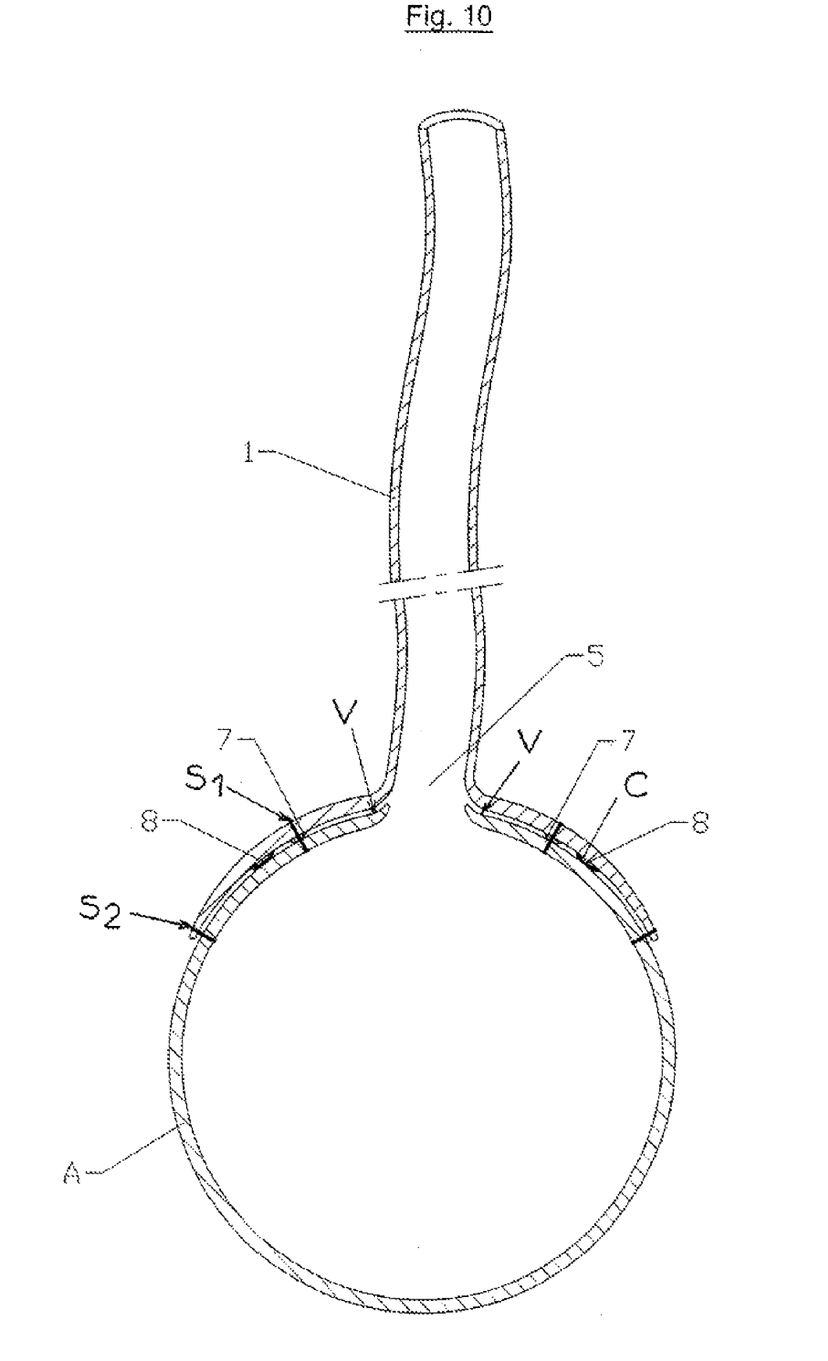
FIG. 10 is a schematic drawing showing an example of attaching the device according to the invention to an arterial vessel.

In a preferred embodiment, collar 2 can be attached to the aorta with two stitches, one of which (S1) will follow colored mark 6 and apply seal 7 to the wall of the aorta, A, the other (S2), being supported by the peripheral edge of collar 2, may seat a second seal 16 and follows the second corresponding colored mark. Between the two lines of sutures S1, S2, biological glue C and/or a haemostatic product injected into cavity 8 provided for that purpose by the two catheters 9a, 9b will complete attachment of collar 2 to aorta A (FIG. 10). At this stage there is no communication between aorta A and prosthetic conduits 1a, 1b, 1c. The prosthetic device is not circulatory.

Communication between aorta A and prosthetic conduits 1a, 1b, 1c at the level of the orifices of collar 5a, 5b, 5c occurs once collar 2 is perfectly attached to the wall of aorta A. This is accomplished using principles of endovascular techniques that do not require any clamping. For example, we cite one of the techniques that might be used to implement this communication.

Figure 12:
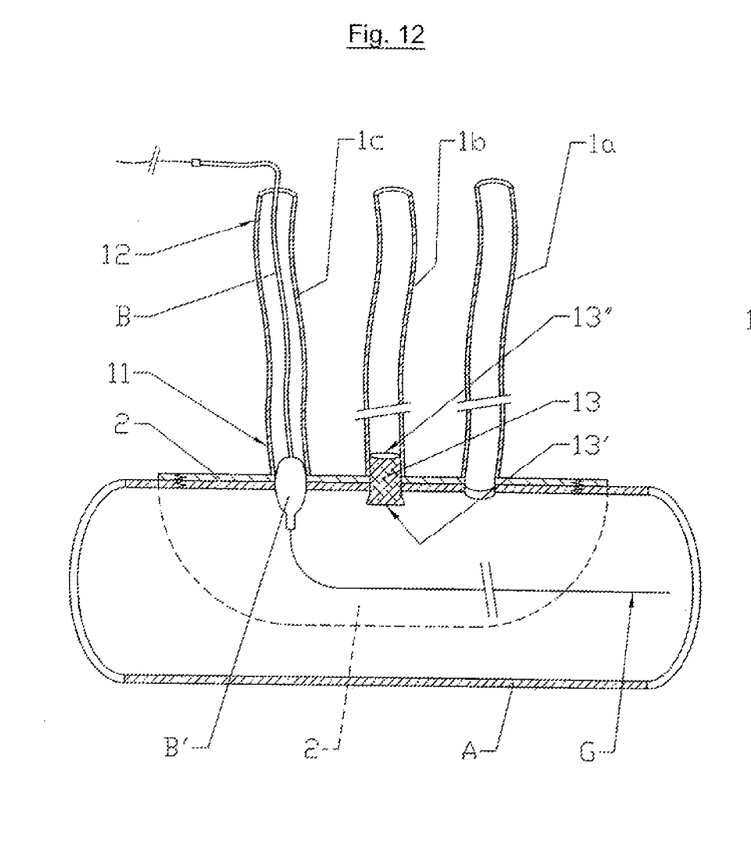
FIG. 12 is a schematic view illustrating the installation of a stent in such a prosthetic device.

A/With a needle introduced through one of the collateral prosthetic branches 1a, 1b, 1c, the wall of the aorta is pierced at the center of the corresponding orifice of this branch and a radiologic guidewire G (FIG. 12) is introduced into the opening made in the aorta.

B/Then, using guide G, balloon B' catheter B is introduced over the guidewire and an orifice is created in the aorta wall opposite the orifice of the prosthetic branch in question by inflating balloon B, which dilates the wall. This orifice can also be effected by introducing a large-diameter catheter having a cone-shaped nose.

C/In the orifice thus created, stent 13, which may or may not be covered, may be deployed, whose role it is to stabilize the orifice and further solidify the connection of the aorta and collar with its branch. This stent 13 may be covered and have a specific shape, for example, preferably, the shape of a rivet or funnel, for improved attachment and opening of the orifice. The spread part, 13', of the stent being on the aorta side, the narrower part, 13", is found in the collateral prosthetic branch. This stent, 13, will help to further isolate the internal suture line, S1, of the circulating part.

In the particular embodiment cited above, where prosthetic conduit(s) 1a, 1b, 1c are intentionally short, this stent can be attached to the proximal end of the tube used to extend the prosthetic conduit(s) to the collateral branches A1, or A2, or A3, that are to be revascularized.

Once the opening is made, a forceps (or clamp) will momentarily hold this prosthetic branch closed until distal anastomosis is completed on the collateral anatomic branch under consideration A1, or A2, or A3.

Communication between the aortic lumen and the other two branches will take place in the same way.

After the preceding steps, blood arrives in branches 1a, 1b, 1c of the prosthetic device. The distal part of these branches is then successively anastomosized with anatomic vessels A1, A2, A3, which must be revascularized according to a conventional surgical technique.

We observe that the prosthetic device according to the invention may have an additional flexible tube (not shown) connected to outer face 3 of collar 2 and of a material identical to that of prosthetic conduits 1a, 1b, 1c, dedicated to the passage of the instruments needed to insert an endoprosthesis into the aorta whenever this presents an aneurysm. This additional tube culminates in an orifice crossing said collar 2.

If revascularization for the occlusion of collateral branches A1, A2, A3 is indicated, the operating procedure just described may be sufficient.

If the branches of the aortic arch are revascularized for an aneurysm (FIG. 11), following revascularization of the first two anatomical collateral branches, we can exclude the arch by means of endoprosthesis 14, by using either the third prosthetic branch of the device not yet anastomosized, or by using the additional tube previously described and provided for that purpose. The branch or tube may be used to introduce the catheter containing the endoprosthesis.

We can also conclude normal revascularization of the third branch, A3, and exclude the aortic arch by means of an endoprosthesis introduced into the femoral pathway. The exclusion can take place at any time given that blood is already present in the collateral branches. The origin of the revascularized branches A1, A2, A3 is generally ligated upstream of the distal anastomosis (these ligatures, L1, L2, L3, are shown schematically in FIG. 11).

Figure 11:
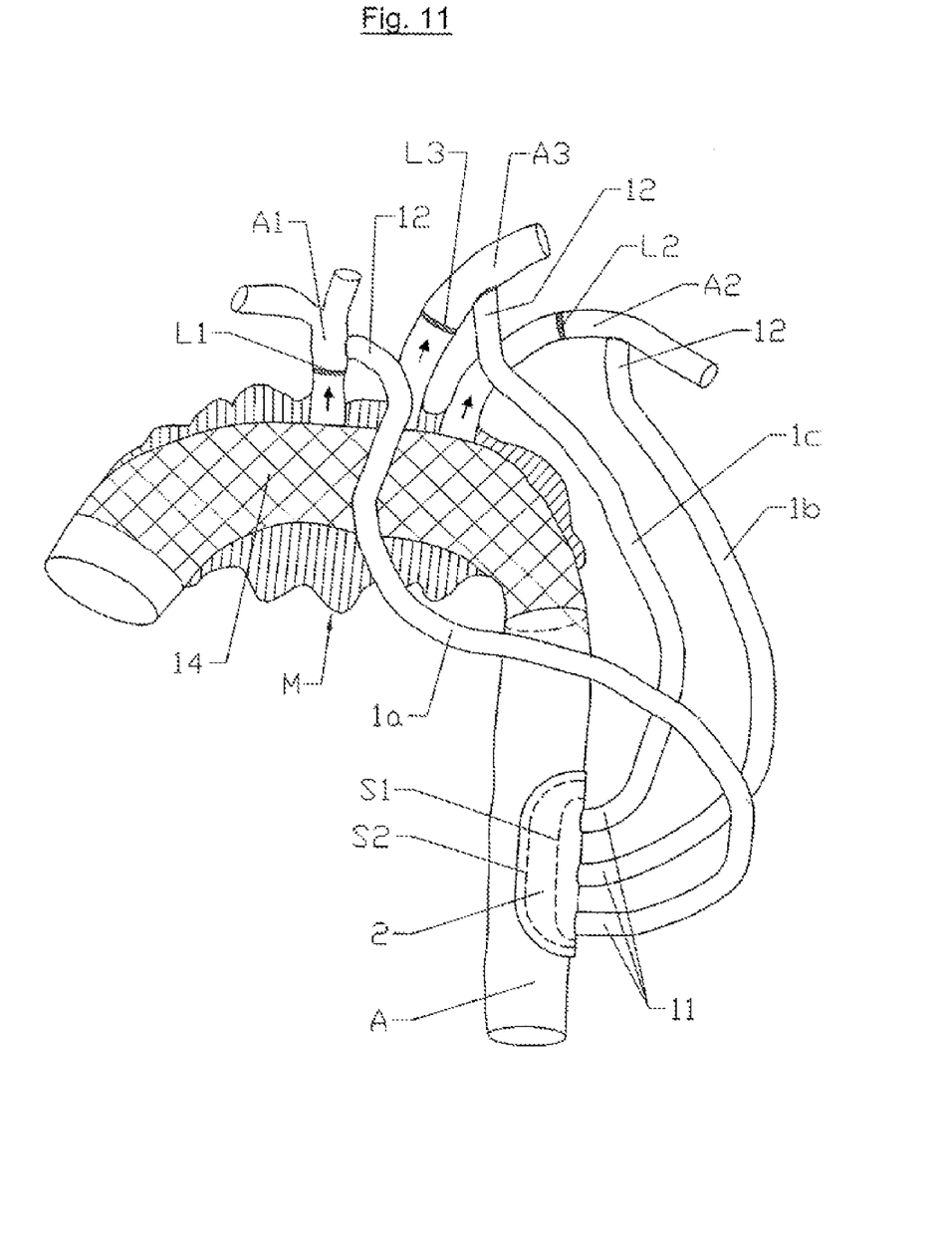
FIG. 11 is a larger scale cross-section showing the attachment of this device to an aorta.

FIG. 11 shows the final result, with collar 2 of the device attached to the aorta (A), prosthetic conduits 1a, 1b, 1c of said device, whose distal parts 12 are anastomosized with collaterals A1, A2, A3 of aorta A, and aortic endoprosthesis 14, which excludes and treats the aneurysm or diseased part M.

We further emphasize that by using this method and the prosthetic device according to the invention, it is possible to perform vascular anastomosis on the aorta or any other vessel without any clamping, partial or total. Along the aortic arch, this avoids extracorporal circulation with hypothermia and circulatory arrest.

This characteristic allows for a very simple operating procedure whose goal is to reduce the impact of surgery and patient mortality. It is no longer necessary to clamp the aorta, and this is especially advantageous for the thoracic aorta and thoraco-abdominal aorta. This simplification of the technique of attaching the prosthetic device also helps to reduce the size of thoracic and/or abdominal incisions when accessing the aorta, or even to do so through videoscopic access of the aorta, which will have the effect of completely eliminating incisions.

The invention claimed is:

1. A prosthetic device for creating a vascular bypass from an arterial vessel, the prosthetic device comprising:
   at least one prosthetic tube;
   a flexible collar having an outer face and an inner face, said collar suitable for application to an outer wall of the arterial vessel, said collar having an orifice zone having at least one orifice therein, the orifice being in communication with the prosthetic tube, said attachment collar having a connection zone arranged around said orifice zone at a distance from the orifice, said connection zone suitable for connection to the outer wall of the arterial vessel, said connection zone having an inner face with an annular cavity extending around said orifice zone, said annular cavity suitable for receiving an injected glue or bioabsorbable haemostatic product so as to attach to the outer wall of the arterial vessel in order to form a leakproof seal.

2. The prosthetic device of claim 1, said inner face of said connection zone having at least one flexible annular leakproof seal extending around said orifice zone.

3. The prosthetic device of claim 1, said annular cavity defined by an annular strip applied to the outer wall of the arterial vessel, said annular strip having a plurality of holes suitable for diffusing the injected glue or bioabsorbable haemostatic product toward the arterial vessel.

4. The prosthetic device of claim 3, said annular strip being of a biological material, said annular strip having lateral edges attached to said inner face of said collar.

5. The prosthetic device of claim 2, said annular cavity positioned away from said annular leakproof seal on a side opposite said orifice zone.

6. The prosthetic device of claim 1, said annular cavity defined by a pair of spaced concentric seals arranged on said inner face of said collar, said annular cavity having at least one opening thereto.

7. The prosthetic device of claim 1, said collar having a flexible seal positioned around and away from said annular cavity on a side of said annular cavity opposite said orifice zone, said flexible seal positioned on said inner face of said cavity.

8. The prosthetic device of claim 2, the annular leakproof seal being a ridge of flexible biocompatible material.

9. The prosthetic device of claim 1, further comprising:
at least one flexible catheter communicating with said annular cavity, the flexible catheter suitable for injecting the biological glue or haemostatic product, the flexible catheter having a proximal end extending through an opening formed through said collar and being accessible on said outer face of said collar.

10. The prosthetic device of claim 9, said at least one flexible catheter comprising a pair of catheters each opening to said annular cavity, one of said pair of catheters suitable for injecting the biological glue into said annular cavity, the other of said pair of catheters suitable for injecting a catalyzing product into said annular cavity.

11. The prosthetic device of claim 2, said orifice zone having a colored annular mark at a periphery thereof, said colored annular mark being visible at said outer face of said collar and corresponding to a location of said annular leakproof seal.

12. The prosthetic device of claim 7, said collar having a colored annular mark on an outer face thereof, said colored annular mark corresponding to a location of said flexible seal.

13. The prosthetic device of claim 1, the orifice being of a circular cross-section.

14. The prosthetic device of claim 1, the orifice being an oval cross-section.

15. The prosthetic device of claim 1, said collar having a shape of a portion of a straight cylinder.

16. The prosthetic device of claim 1, said collar having a shape of a bent cylinder.

17. The prosthetic device of claim 1, further comprising:
an additional tube connected to said collar so as to open through said collar, said additional tube suitable for allowing an operating instrument to pass therethrough.

18. The prosthetic device of claim 1, further comprising:
at least one stent installed in the prosthetic tube in an area adjacent the orifice of said collar.

19. The prosthetic device of claim 1, further comprising:
at least one prosthetic conduit connected to said at least one prosthetic tube and extending therefrom, the prosthetic conduit suitable for connection to a branch of the arterial vessel being revascularized, the prosthetic conduit having a length greater than a length of the prosthetic tube.

20. The prosthetic device of claim 19, the prosthetic conduit being connected to a stent positioned within the prosthetic tube.

* * * * *